US006706479B2

(12) United States Patent
Saraf et al.

(10) Patent No.: US 6,706,479 B2
(45) Date of Patent: Mar. 16, 2004

(54) BIO-CHIP, PHOTOLUMINESCENT METHODS FOR IDENTIFYING BIOLOGICAL MATERIAL, AND APPARATUSES FOR USE WITH SUCH METHODS AND BIO-CHIPS

(75) Inventors: Ravi F. Saraf, Blacksburg, VA (US); Sanjun Niu, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 21 days.

(21) Appl. No.: 09/870,986

(22) Filed: Jun. 1, 2001

(65) Prior Publication Data

US 2002/0042070 A1 Apr. 11, 2002

Related U.S. Application Data
(60) Provisional application No. 60/286,525, filed on Apr. 27, 2001, and provisional application No. 60/237,677, filed on Oct. 5, 2000.

(51) Int. Cl.[7] .............................. C12Q 1/68; C12P 19/34; C30B 21/02; B32B 15/00; H01L 31/00
(52) U.S. Cl. .......................... 435/6; 435/91.1; 428/209; 117/68; 250/214.1
(58) Field of Search ................. 117/68; 250/214.1; 428/209; 435/6, 91.1

(56) References Cited

U.S. PATENT DOCUMENTS

| | | | |
|---|---|---|---|
| 4,820,649 A | | 4/1989 | Kawaguchi et al. |
| 5,194,393 A | | 3/1993 | Hugl et al. |
| 5,552,272 A | | 9/1996 | Bogart |
| 5,593,867 A | | 1/1997 | Walker et al. |
| 5,629,214 A | | 5/1997 | Crosby |
| 5,707,799 A | | 1/1998 | Hansmann et al. |
| 5,711,915 A | | 1/1998 | Siegmund et al. |
| 5,786,139 A | | 7/1998 | Burke et al. |
| 5,831,259 A | * | 11/1998 | Charra .................... 250/214.1 |
| 5,837,196 A | | 11/1998 | Pinkel et al. |
| 5,849,547 A | | 12/1998 | Cleuziat et al. |
| 5,858,653 A | | 1/1999 | Duran et al. |
| 5,955,377 A | | 9/1999 | Maul et al. |
| 5,962,218 A | * | 10/1999 | Leland ........................... 435/6 |
| 5,981,185 A | | 11/1999 | Matson et al. |
| 6,045,996 A | | 4/2000 | Cronin et al. |
| 6,060,237 A | | 5/2000 | Nguyen et al. |
| 6,117,529 A | * | 9/2000 | Leising ......................... 428/209 |
| 6,241,819 B1 | * | 6/2001 | Bhargava ..................... 117/68 |
| 6,284,503 B1 | * | 9/2001 | Caldwell et al. |
| 6,297,018 B1 | | 10/2001 | French et al. |

FOREIGN PATENT DOCUMENTS

WO      WO02/29102      4/2002

OTHER PUBLICATIONS

Fixed Polarizer ellipsometry for simple and sensitive detection of thin films generated by specific molecular interactions: applications in immunmoassays and DNA sequence detection, Clinical Chemistry 2031–2035 (1998) R. M. Ostroff, D. Maul, G. R. Bogart, S. Yang, J. Christian, D. Hopkins, D. Clark, B. Ttotter, and G. Moddel.

Processing of cDNA and Genomic Kilobase–Size Clones for Massive Screening, Mapping and Sequencing by Hybridiziatiom, Research Report, Snezana Drmanac and Radoje Drmanac; Argomme National Laboratory, Argonne, Il, Bio–Techniques vol. 17 No. 2 (1994).

Absorption of Avidin on Microfabricated Surfaces for Protein Biochip Applications, Biotechnology and Bioengineering, vol. 73, No. 4 (May 20, 2001).

Genetic Engineering of a Single–Chain Antibody Fragment for Surface Immobilization in an Optical Biosensor, Biosensors & Bioelectronics, vol. 13, No. 3–4 (Mar. 1, 1998).

High–Throughput Assays on the chip based on metal Nano–Cluster Resonance, Journal of Pharmaceutical and Biomedical Analysis, vol. 24 No. 5–6 (Mar. 2001).

Immobilization of Nucleic Acids at Solid Surfaces: Effect of Oligonucleotide Length on Layer Assembly, Biophysical Journal, vol. 79, No. 2 (Aug. 2000).

A Steptavidin Surface on Planar Glass Substrates for the Detection of Biomolecular Interaction Analytical Biochemistry, vol. 282, No. 2, (Jul. 1, 2002).

Considerations for the Quantitative Transductioni of Hybridization of Immobilized DNA, Analytica Chimica Acta, vol. 400 No. 1–3, (Nov. 22, 1999).

Direct Bioelectrochemical Monitoring of Choline Oxidase Kinetic Behavior in Langmuir–Blodgett Nanostructure, Bioelectrochemistry and Bioenergetics, vol. 46, No. 1 (Aurg. 1998).

Immobilization of Ultra–Thin Layer of Monoclonal Antibody on Glass Surface, Journal of Chromatography, vol. 566, No. 2 (May 31, 1991).

(List continued on next page.)

Primary Examiner—Stephanie W. Zitomer
Assistant Examiner—Arun K. Chakrabarti
(74) Attorney, Agent, or Firm—Whitham, Curtis & Christofferson, P.C.

(57) ABSTRACT

A method detects binding of molecules, advantageously without tagging molecules in the sample. A sensor is used in which is included a single stranded nucleic acid sequence and a photoluminescent material in respective layers. After the sensor is exposed to a biological sample for sufficient time for its single stranded nucleic acid sequence to bind to a material of interest, photoluminescence from the sensor can be measured. An apparatus for tagging-free detection of binding of molecules also is provided. Methods of making tagging-free sensors are provided. Also, tagging-free methods to detect binding of antigens and related devices are disclosed.

22 Claims, 14 Drawing Sheets

OTHER PUBLICATIONS

Detection of Conformation Changes in a Immobilized Protein Using Surface Plasmon Resonance, Anaylitcal Chemistry, vol. 70, No. 10 (May 15, 2998).

Montioring of the Refolding Process for Immobilized Firefly Luciferase with a Biosensor Based on Surface Plasmon Resonance, Journal of Biochemistry vol. 129, No. 1 (Jan. 2001).

Immunosensors Technology and Opportunities in Laboratory Medicine, Clinical Chemistry, vol. 42, No. 2 (1996).

Optical Biosensors for Real–Time Measurement of Analytesin Blood Plasma, Biosensors and Bioelectronics, vol. 17 No. 8 (Aug. 2002).

Chemiluminescent Immunoenzyme Biosensor with a thin–layer Flow–through Cell: Application for Study of a Real–Time Bimolecular Antigen–Antibody Interaction, Biosensors & Bioelectronics, vol. 11, No. 9 (1996).

\* cited by examiner

IN-SITU COMPOSITE
1. ION EXCHANGE
2. PARTICLE SYNTHESIS
3. SURFACE REGENERATION

LITHOGRAPHY
1. SURFACE MODIFICATION AT SELECTED REGIONS

DNA GRAFTING
1. SELECTIVE ssDNA GRAFTING

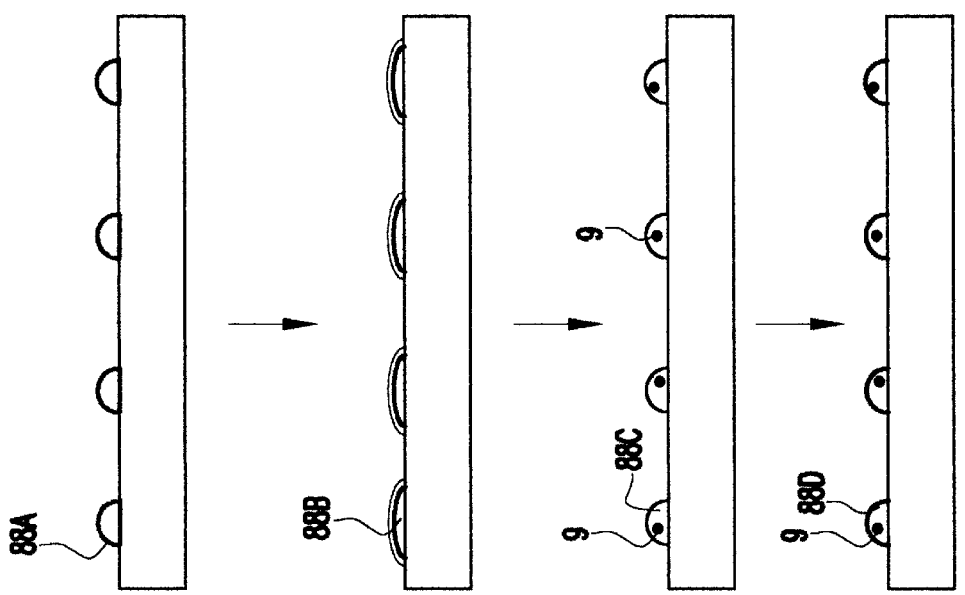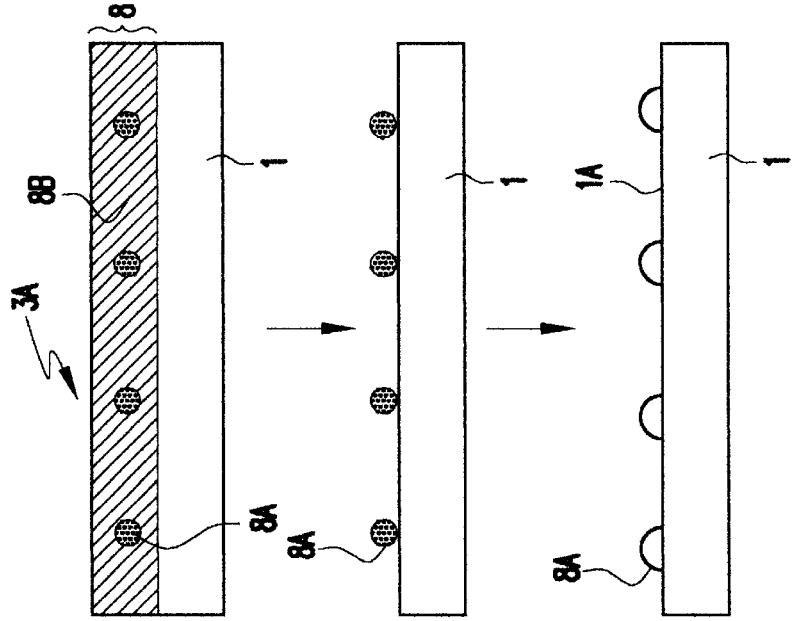

HYBRIDIZATION

BIO-CHIP, PHOTOLUMINESCENT METHODS FOR IDENTIFYING BIOLOGICAL MATERIAL, AND APPARATUSES FOR USE WITH SUCH METHODS AND BIO-CHIPS

This application claims the benefit of provision applications Nos. 60/286,525 filed Apr. 27, 2001 and 60/237,677 filed Oct. 5, 2000.

FIELD OF THE INVENTION

The invention generally relates to nucleic acid, and more particularly, to binding of single stranded nucleic acid with biological material of interest in a sample to identify the material.

BACKGROUND OF THE INVENTION

Nucleic acids such as deoxyribonucleic acid (DNA), ribonucleic acid (RNA) and protein nucleic acid (PNA) are fundamental components of matter of living organisms. Nucleic acids generally speaking consist of certain constituent parts, or base pairs. The permutations in which these base pairs may be arranged is vast. Nucleic acid sequence analysis, i.e., determining the identity and sequence of the base pairs of a nucleic acid sample, is an important technology. Deciphering nucleic acid sequences is important for disease diagnosis, drug design and understanding of various biological mechanisms. Before 1996, traditional methods laboriously "read" the gene sequencing one base pair at a time.

Around 1996, Affymetrix developed a massively parallel sequencing approach, using a DNA chip with which several base pairs can be read simultaneously. A monolayer of specific single stranded DNA (ssDNA) fragments is assembled on an array of pixels (~1–100 $\mu m^2$). The type of ssDNA may change from pixel to pixel. These ssDNA fragments act as "chemical tweezers" to pick the specific complementary tagged ssDNA from the sample to form double stranded DNA (dsDNA), i.e., a hybridization process occurs. The hybridized region is observed by a fluorescent label applied to the DNA in the sample before exposure to the ssDNA probe fragments. The process is speedier than single-base-pair methods, is specific, can analyze multiple nucleotide sequences, simultaneously can process hundreds of gene sequences and their alterations, and uses advantageously small chips. Practical applications of the parallel sequencing technology include: Affymetrix' study of p53 gene malfunction (i.e., mutation) responsible for cancer (especially breast cancer); Merck's study of changes in DNA sequencing as the cell beings to rapidly proliferate (to understand tumor formation); Incyte Pharmaceutical's disease-specific chips for drug design. Also, massively parallel, quick, sensitive and accurate bio-chip methods may boost the Human Genome Project.

However, Affymetrix' approach tags unknown to-be-sequenced DNA with a fluorescent dye—altering the sample so that it generally cannot be reused for other tests. Also, because the Affymetrix chip at each pixel has about at least a 5% error margin, the chip includes many repeated pixels, to manage the error margin. The fabrication process for Affymetrix' chip is expensive, requiring lithographic technique.

DNA sequencing and other protein identification techniques, especially speedy parallel approaches, have important practical applications, such as disease diagnosis, drug design, genetic and cancer screening, deciphering and functional study (such as mutation, gene expression) of genetic code, understanding various biological mechanisms, crime detection, etc. Although advances in DNA sequencing and other protein sequencing technologies have been made in recent years, such procedures still limit and delay workers in the art awaiting sequencing results. Those whose work relies on DNA sequencing and other protein sequencing would be helped by expedited rapidity of sequencing, simplified sequencing, and/or enhanced precision and accuracy. Also, a small portable device useable in a doctor's office to check, for example, if a patient may eventually develop cancer or how fast the body is likely to break down a specific anti-cancer drug have been generally theorized as of interest. For all these applications, a tool that can perform a nucleic acid analysis of a small size sample for several specific genes (at low concentrations) is highly desirable, but not conventionally provided. Rather, the conventional bio-chip methods undesirably require tagging of the sample plus other disadvantages (such as expensive manufacturing methods, uncertainty in the number of fragments per pixel, etc.).

SUMMARY OF THE INVENTION

It therefore is an object of this invention to provide methods and products for detecting the hybridization state of a nucleic acid molecule, without needing to tag the sample. The invention can be used to perform sequence analysis of unknown nucleic acids, such as DNA sequences. Several genes can be probed simultaneously. Sequencing according to the invention is relatively simple and quick, while providing precise and accurate sequencing information. The invention provides a bio-chip and other products for simultaneously analyzing one or more specific nucleic acid fragments (such as genes) in a solution.

In order to accomplish these and other objects of the invention, the present invention in a preferred embodiment provides a tagging-free method to detect binding of molecules, comprising the steps of: (A) providing a sensor comprised of a first layer including a single stranded nucleic acid sequence and a second layer including a photoluminescent material; (B) exposing said sensor to a biological sample for sufficient time for said single stranded nucleic acid sequence to bind to a material of interest in said biological sample; (C) exposing said sensor to light and measuring photoluminescence from said sensor. In a particularly preferred inventive tagging-free method, the measuring step includes sensing photoluminescent light from the second layer when ultraviolet light with wavelength in the range of 200–700 nm is applied to the first layer. In an especially preferred embodiment, the wavelength of the ultraviolet light applied is in the range of 260–265 nm. In an especially preferred embodiment, the first layer is positioned on a first side of the second layer, and said measuring step measures photoluminescence from a second side of said second layer. In a further embodiment, said second side is opposite said first side on said second layer. In another embodiment that is preferred, said first layer is positioned on a first side of said second layer, and said measuring step measures photoluminescence reflected from said first side of said second layer.

In another preferred embodiment, the invention provides a tagging-free sensor comprising a first layer including a single stranded nucleic acid sequence and a second layer including a photoluminescent material.

In another preferred embodiment, the invention provides an apparatus for tagging-free detection of binding of molecules, comprising: a light source; a sensor having a nucleic acid layer and a photoluminescent layer; and a photoluminescence detector. In especially preferred embodiments, the light source is an ultraviolet light source, an infrared light source, or a visible light source. In other especially preferred embodiments, the detector is a light detector in the infrared to ultraviolet range. Where an ultraviolet light source is used, the ultraviolet light source in a particularly preferred embodiment provides ultraviolet light at a range of about 260–265 nm.

In another preferred embodiment, the invention provides a method of making a tagging-free sensor, comprising: contacting a single stranded nucleic acid sequence with a photoluminescent material. A particularly preferred embodiment of such an inventive method includes depositing photoluminescent material on a substrate to form a surface, and thereafter modifying the surface by ion exchange treatment with a metal salt, followed by ion-embedding, followed by exposing the ion-embedded material to reactive media to form photoluminescent particles.

In the above-mentioned methods, products and apparatuses, a particularly preferred embodiment of the invention uses DNA, RNA and/or PNA as the single stranded nucleic acid. In an especially preferred embodiment, the first layer comprises an ssDNA monolayer. In a particularly preferred embodiment, the sensor comprises ssDNA as said first layer grafted onto the second layer.

In a preferred embodiment, the nucleic acid sequence is between 5 and 200 base pairs. In an especially preferred embodiment, the sequence is about 25 base pairs. Another particularly preferred embodiment provides a discontinuous first layer comprising different nucleic acid sequences in different sections of said first layer.

Further, another preferred embodiment of the invention provides a tagging-free method to detect binding of antigens, comprising the steps of: (A) providing a sensor comprised of a first layer including an antibody and a second layer including a photoluminescent material; (B) exposing said sensor to a biological sample for sufficient time for said antibody to bind to an antigen of interest in said biological sample; (C) measuring photoluminescence from said sensor. In a particularly preferred embodiment, the first layer is discontinuous and comprises different antibodies.

In another preferred embodiment, the invention provides an apparatus for tagging-free detection of antibody binding, comprising: a light source; a sensor having a first layer including an antibody and a second photoluminescent layer; and a light detector.

Additionally, another preferred embodiment of the invention provides a tagging-free sensor comprising a first layer including an antibody and a second layer including a photoluminescent material. In a particularly preferred embodiment, the first layer is discontinuous and comprises different antibodies. In another especially preferred embodiment, different known antibodies are included.

Further detailed embodiments of the above-mentioned inventive methods, products and apparatuses are as follows.

Another particularly preferred embodiment of the invention in the second layer uses aromatic polymers, doped or undoped metal oxides, sulfides, selenides, arsenides, tellurides, and/or nitride and phosphide nanocomposites. In another preferred embodiment, the second layer may comprise a matrix material, with said photoluminescent material associated with said matrix material. In a further preferred embodiment, said photoluminescent material is embedded in said matrix material. In an especially preferred embodiment, the second layer comprises polystyrene. In an especially preferred embodiment, the second layer comprises photoluminescent particles in a polymer matrix. In a further preferred embodiment, the photoluminescent particles may be doped or undoped compounds selected from the group consisting of group II and group VI. In another preferred embodiment, as such a compound is used doped or undoped zinc sulfide. Another especially preferred embodiment is one in which the second layer comprises a nanocomposite. In a further preferred embodiment, the second layer comprises a thin-film or a support. In another preferred embodiment, the second layer comprises a polymer. In another preferred embodiment, the second layer has fluorescence when excited by light with a wavelength in the 200–700 nm range.

BRIEF DESCRIPTION OF THE DRAWINGS

The foregoing and other objects, aspects and advantages will be better understood from the following detailed description of the preferred embodiments of the invention with reference to the drawings, in which:

FIGS. 15(a)–(g) show an exemplary process flow for making a nanoparticle array according to the invention.

DETAILED DESCRIPTION OF THE PREFERRED EMBODIMENTS OF THE INVENTION

Figure 1:
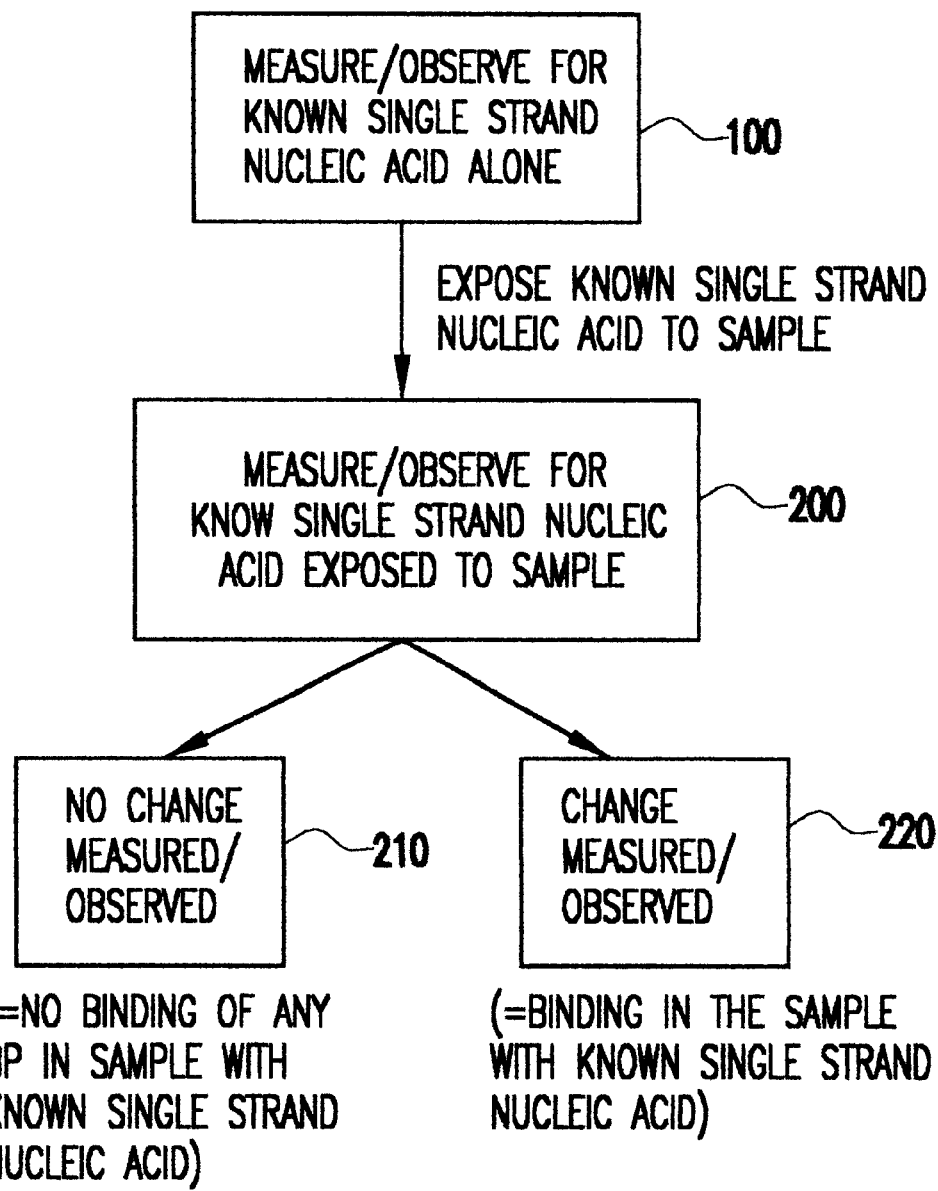
FIG. 1 is a flowchart depicting a method according to the present invention.

In a first preferred embodiment, of which FIG. 1 is exemplary, the invention accomplishes nucleic acid (such as DNA, RNA or PNA) or protein sequence analysis without tagging (such as fluorescent dye tagging), and provides products and apparatuses useable for such tagging-free sequencing. Binding of molecules to a single stranded nucleic acid sequence can be detected without using conventional tagging. The invention uses a material that is photoluminescent, which broadly includes a material that glows at any wavelength or that luminesces because of photons. The invention uses application of light, and the light input may be ultraviolet, visible, infrared or other light, without limitation.

In an exemplary embodiment of such an inventive tagging-free method, a single stranded nucleic acid material of known sequence is provided. Examples of the single stranded nucleic acid material are DNA, RNA and PNA. The single stranded nucleic acid sequence may be of any length, with a preferred example being about 25 bp; however, the single stranded nucleic acid could range from 5 to 200 bp.

As seen with reference to FIG. 1 of an exemplary detection system according to the invention, a measurement or observation 100 optionally may be made for a known single stranded nucleic acid, alone. A numerical measurement is not necessarily required, and a baseline measurement in the nature of a calibrating measurement or observation is within the present invention. The present invention is based on differential (rather than absolute) measurements or observations. In some embodiments, measurement or observation 100 may be eliminated.

After measurement/observation 100, the known single stranded nucleic acid sequence is then exposed to a biological sample, such as a sample containing biological material for which information is desired as to whether material complementary to the known single stranded nucleic acid sequence is contained therein. For example, the sample may comprise denatured DNA, RNA or PNA of unknown identity.

For contacting the sample with the single stranded nucleic acid, known methods may be used, such as providing the single stranded nucleic acid on a bio-chip and pipetting a small amount of the sample solution into a well in the bio-chip. The conditions of contacting the biological sample with the known single stranded nucleic acid material are those permitting binding of the known single stranded nucleic acid material with at least one protein or nucleotide in the biological sample to form a complex, such as hybridizing conditions. Hybridizing conditions are known to those working in the art. Upon such exposure of the known single stranded nucleic acid sequence to the biological sample, binding, hybridizing and formation of a complex occur if complementary material is contained in the biological sample. Software is known to optimize hybridizing conditions, by varying temperature, salt concentration, etc.

After the exposure procedure, an observation or measurement 200 is carried out, to observe or measure change (if any) in photoluminescence. For example, when providing single stranded nucleic acid on a bio-chip, the bio-chip may be illuminated with light at a wavelength at which the single stranded nucleic acid and the double stranded nucleic acid differentially absorb. Depending on what has occurred in the exposure process, no change 210 may be measured/observed, or change 220 may be measured/observed. If no change 210 is found, it can be concluded that the sample lacks a sufficiently complementary material to bind to the known single stranded nucleic acid sequence.

If change 220 is found, it can be concluded that a sufficiently complementary material in the sample has bound to the known single stranded nucleic acid sequence. From the identity of the known single stranded nucleic acid sequence, the likely identity of the complementary bound material can be inferred. The amount of change 220 will vary depending upon the degree of complementarity between the single stranded DNA and the biological material. The change 220 is a function of the change in photoluminesce that can be measured from a support underlying the single stranded DNA. As more and more biological material from the sample is bound to the single stranded DNA, greater and greater differences in the detectible luminescence will result because of changes in the physical characteristics of the nucleic acid between its single stranded and bound state.

In a preferred embodiment of the invention, a known single stranded nucleic acid sequence is provided on a substrate, probe, bio-chip or other solid product, and the biological sample is contacted in liquid form with the solid product. In other embodiments of the invention, the unknown or to-be-sequenced biological material may be provided on a substrate, probe, bio-chip or other solid product and contacted with a liquid probe comprising sensor particles each including a known single stranded nucleic acid sequence attached to a photoluminescent material.

The inventive methods and products may be used to sequence nucleic acid molecules (such as DNA, RNA or PNA) or other proteins. For example, one or more specific DNA fragments (i.e., a gene) of unknown identity and sequence may be analyzed. The source materials for a biological sample to test are not particularly limited and may be any nucleic acid or protein-containing biological materials (such as blood, tissue, fingernail clippings, etc.). Raw biological material, such as blood, generally may be processed into testable fragments and put into solution by methods known to those skilled in the art.

The single stranded nucleic acid sequence used in the present invention is not particularly limited in the form in which it is used, and a form such as a monolayer may be used. A monolayer is particularly preferred.

In a preferred embodiment, the single stranded nucleic acid of the present invention is attached to a photoluminescent material. A preferred example of the attachment is by grafting. "Grafting" may include covalently bonding a portion of the single stranded nucleic acid to the photoluminescent material (e.g., by an amine linkage from lysine or histidine), or it may include physical adsorption on the photoluminescent material, or other joining mechanism that associates the single stranded nucleic acid and the photoluminescent material in a manner which leaves a portion of the single stranded nucleic acid free to bond to other biological materials of interest. Examples of the photoluminescent material include, without limitation, an optically active thin film, aromatic polymers, matrix materials that include metal oxides or sulfides such as ZnS doped with Mn, etc.

By way of non-limiting example, in an embodiment in which a single stranded nucleic acid monolayer is grafted to an optically active thin film, when the single stranded nucleic acid monolayer is exposed to light, the amount of emitted light from the attached optically active thin film depends on absorption by the single stranded nucleic acid layer. When the single stranded nucleic acid layer comes in contact with a complementary molecule, the single stranded nucleic acid layer binds to the complementary molecule. Particularly, ssDNA converts to dsDNA. The binding of the single stranded nucleic acid causes the intensity of fluorescent emission from the attached photoluminescent material to change. Where ssDNA is used as the single stranded nucleic acid sequence, the observable fluorescence intensity for ssDNA versus dsDNA differs (because the absorption of ssDNA is higher than dsDNA) in the 260 nm range. Fluorescence intensity is higher for the bound form (such as a converted dsDNA form) and this fluorescence intensity can be observed to confirm the presence of the complementary sequence in the sample being tested.

For preferred materials according to the invention, e.g., polystyrene as the photoluminescent layer attached to ssDNA, the change in intensity of the photoluminescence when the ssDNA converts to dsDNA differs by only about 2–4%, so that studying the intensity would not be particularly dramatic. However, the present inventors have made the important recognition that at 260–265 nm, not only the absorption changes, but the refractive index changes, because of which, the reflection (reflectivity) changes. The amount of light reaching the polystyrene attached to the DNA may change by as high as 200%, for the following reasons.

DNA absorbs generally in the 260–265 nm range (ultraviolet), and shining such radiation on an (unbound) single stranded nucleic acid top layer results in absorption, reflection and scattering of the radiation. The left-over transmitted radiation travels into the photoluminescent material (such as polystyrene) causing it to give out radiation at a different wave length. For example, the photoluminescence in polystyrene is at about 325 nm. However, if the single stranded nucleic acid is bound so that it becomes double stranded, the nucleic acid now absorbs, scatters and reflects a different amount of excitation wavelength, so that the amount of radiation experienced by a photoluminescent underlying layer differs from the case before binding occurred. Correspondingly the photoluminescent material gives out different photoluminescence intensity. The refractive index changes, because of which, the reflection (reflectivity) changes. The amount of light reaching the photoluminescent material underneath may change by 200% or more. This is primarily due to the refractive index changes, because of which, the reflection (reflectivity) changes, resulting in significant change with respect to the excitation light into the photoluminescent layer. Thus, studying the amount of light from the photoluminescent material attached to the nucleic acid sequence provides a dramatically-different result for unbound versus bound nucleic acid sequences.

Figure 2A:
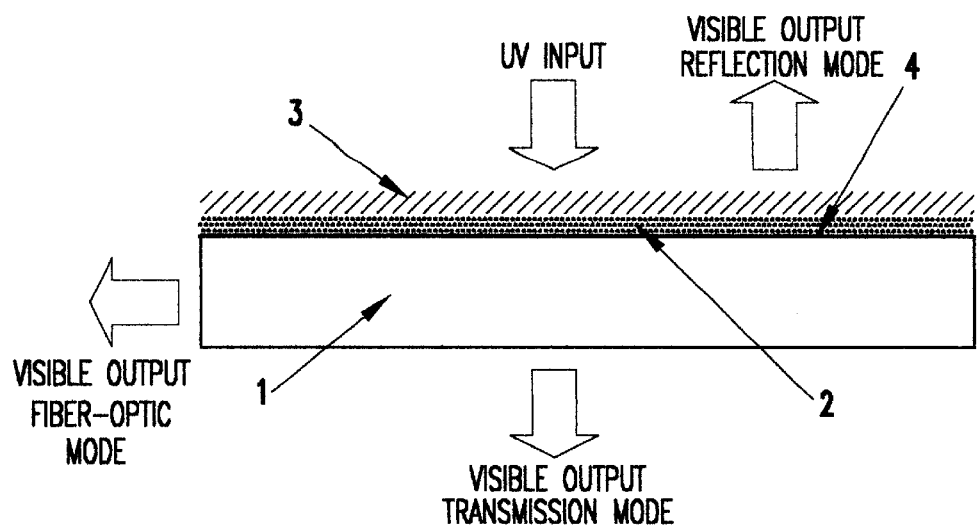
FIG. 2(a) is a cross-sectional view of a device according to the invention.
Figure 2B:
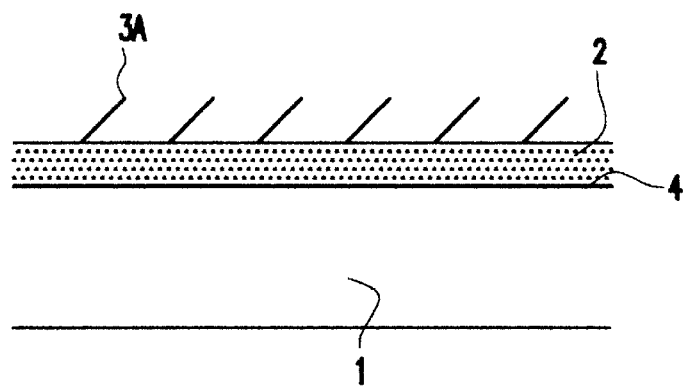
FIGS. 2(b) and 2(c) are enlarged views of part of FIG. 2(a), with FIG. 2(b) showing unbound single stranded nucleic acid material according to the invention and FIG. 2(c) showing bound nucleic acid material according to the invention.
Figure 2C:
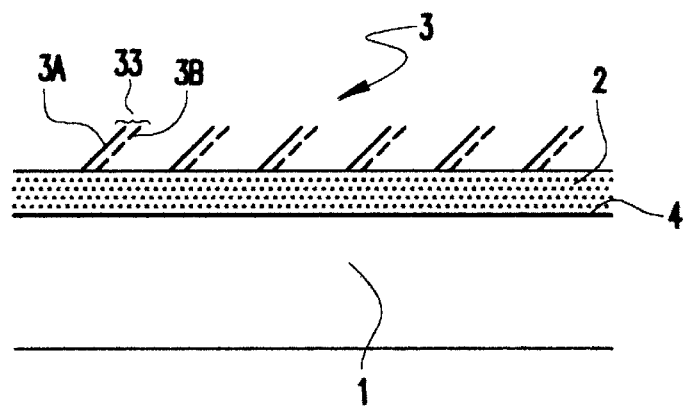

Part of a bio-chip device that is an exemplary form of the invention is shown in FIG. 2(a). The device of FIG. 2(a), in which optically active layer 2 comprises a photoluminescent material such as a nanocomposite or a photoluminescent polymer, may be used as follows The nanocomposite which is a photoluminescent material may be provided in a matrix material, with the matrix material optionally being photoluminescent at the excitation wavelength. FIG. 2(b) shows an enlarged view of part of FIG. 2(a), showing each single stranded nucleic acid sequence 3a of which layer 3 is comprised. In one example of using a device according to the invention, and with reference to FIG. 2(c), the device is exposed to biological sample material complementary to single stranded nucleic acid layer 3 such that conversion of single stranded nucleic acid sequences 3a to a double stranded nucleic acid form 33 occurs by binding with a complementary sequence 3b in the sample, leading to change in input (i.e., excitation) light incident into the photoluminescent layer. The change in the incident light to the photoluminescent layer occurs due to the change in reflectivity, absorption and scattering in the DNA layer as it converts from single stranded to double stranded. Thus, as a result of the binding that is conversion from single stranded to double stranded causes a change in the emitted photoluminescent light intensity. This change in intensity of the emitted photoluminescent light may be recorded, such as by a confocal microscope via a CCD camera, or by fiber-optics. When an integrated optics approach is used, on-line measurement may be done during the hybridization process in solution. On-line embodiments of the invention may be used to probe several genes simultaneously.

In a preferred embodiment, an example of using a device according to FIG. 2(a) is to provide ssDNA of known sequence as the single stranded nucleic acid on the device and then to immerse the device in a solution of various unknown nucleic acid fragments. If there is a complementary pair in the solution to the ssDNA on the device, hybridization will occur, and the ssDNA layer on the device will convert from ssDNA to dsDNA. The invention permits probing whether such a conversion from ssDNA to dsDNA has occurred, to determine if the particular gene (complementary to known ssDNA on the device) exists in a biological sample solution. After reading the photoluminescence for the device contacted with the sample, any bound materials from the sample can be loosened using techniques known to those skilled in the art, and used in other testing or applications.

Probing according to the invention is a measurement of change in photoluminescent light, as generally shown in FIG. 3, which relates to absorption for an inventive method according to FIG. 1 or inventive device according to FIG. 2(a). With reference to FIG. 3, $I_0$ is the intensity of incident UV light at wavelength 265 nm (which is nominally the absorption maxima of DNA). As the UV radiation is absorbed by the layer of photoluminescent material 2, the photoluminescent particles emit visible light of intensity $I_1$, $I_2$ or $I_3$ (which represent output intensity with no DNA graft (i.e., DNA immobilized on the surface by at least one covalent bond). If $\Delta I = I_2 - I_3$ can be measured, the occurrence of any hybridization reaction can be determined. The measurement of $\Delta I$ can be performed in-situ in the solution because the attenuation of $I_0$ due to absorption by the solution is constant and absorption by DNA and solution in the visible range is negligible.

Figure 3A:
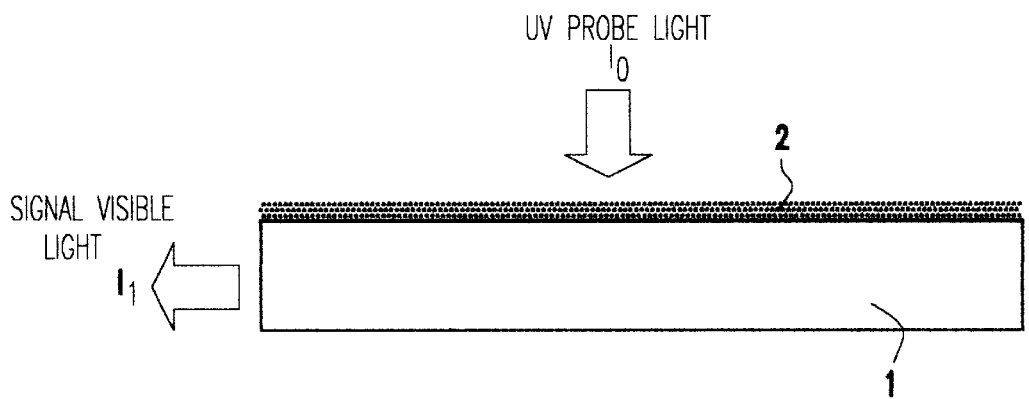
FIGS. 3(a), (b) and (c) together are a series of cross-sectional views showing probing according to the invention.
Figure 3B:
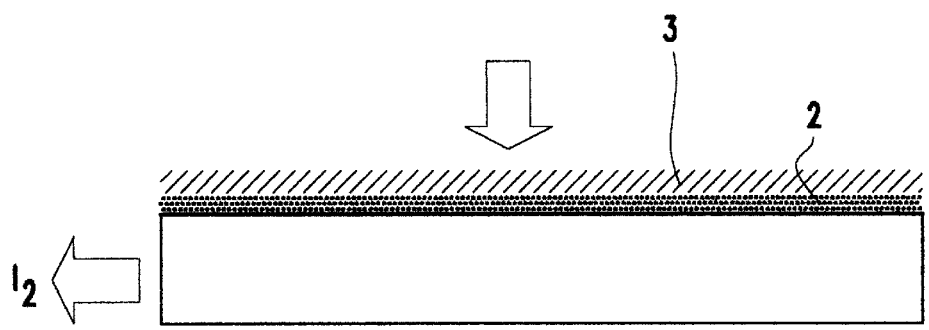
Figure 3C:
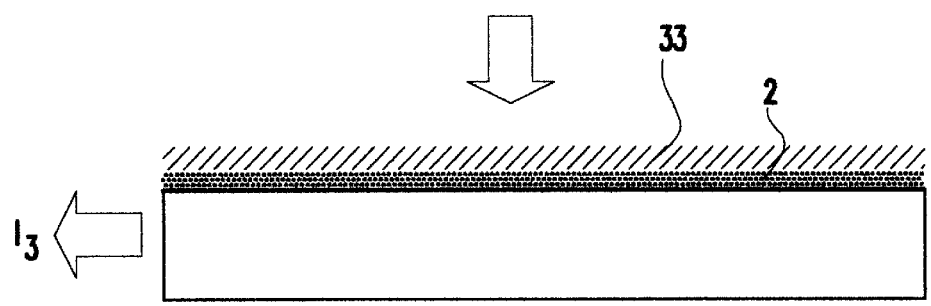

Probing is depicted in FIGS. 3(a), (b) and (c), for the device shown in FIG. 2(a), in a fiber optics mode. $I_1$ in FIG. 3(a) is the photoluminescent intensity from optically active layer 2 which in this example is a nanocomposite for incident UV radiation, 10. The output intensity is reduced to $I_2$ on deposition of ssDNA 3 (FIG. 3(b)) that further reduces UV radiation intensity incident on the optically active layer 2 which is a nanocomposite. The intensity is further reduced when the ssDNA 3 is hybridized to form dsDNA 33 (FIG. 3(c)). The resultant photoluminescent intensity for the device according to FIG. 3(c) is $I_3$. The relevant signal is $\Delta I = I_2 - I_3$.

The device of FIG. 2(a) optionally contains a reflective layer such as gold layer 4 to enhance reflection, depending on the end use. An optional reflective layer is preferably composed of a non-oxidizing material, of which gold is a preferred example. For example, as shown in FIG. 2(a), in the reflection mode, a layer of reflective gold 4 deflects the visible light produced by the photoluminescent material on the top side of the device. In the transmission mode (primarily for device characterization), the gold layer 4 of FIG. 2(a) may be omitted and the visible photoluminescent light may be detected on the other side of the sample. For the fiber optics mode, the gold layer 4 is not needed.

It will be appreciated that sequencing according to the invention may be accomplished without any tagging of the DNA to be tested. This no-tagging feature will allow probing "before" and "after" structure of DNA when subjected to a stimulus. For example, mutation of a gene due to UV radiation can be analyzed by the disclosed DNA chip. A probe according to the invention can probe kinetics of the mutation processes, location of the mutation and, importantly (in the presence of a drug) evaluate the role of the drug-action on inhibition or acceleration of certain mutation processes.

In an alternative embodiment, on-line integrated optics may be used for DNA sequencing according to the invention. In such a configuration, the device may be immersed in a solution to measure both the identity of a specific gene sequence and its hybridization kinetics.

The invention also in a further embodiment may be used to probe DNA "before" and "after" physical or chemical treatment, which may be particularly useful for drug design applications.

In addition to DNA gene sequencing applications and other above-mentioned applications, other uses of the photoluminescent embodiments of the invention include applications that may not be possible for devices using tagging methods. Further, because probes according to the invention may be large area devices, they may be used to separate known sequences from a mixture of single-strand nucleic acid fragments at high precision and sensitivity. Because sensors according to the invention may be made on-line, sensors according to the invention have applications as on-line sensors for PCR.

Devices comprising known single stranded nucleic acid sequences for use in practicing the invention may be easily fabricated, such as by the method shown in FIGS. 4(a) through (d). Examples of a device according to the present invention are a probe, a bio-chip, and other products useable in tagging-free sequencing.

For use in the present invention, known single stranded nucleic acid sequences of length may be used, with sequences of length from about 5 bp to about 200 bp being preferred, and a sequence of about 25 bp being most preferred.

To make an exemplary device according to the present invention, a single stranded nucleic acid sequence (preferably of known sequence) may be attached to a photoluminescent material. Attachment techniques for nucleic acids are known to those skilled in the art, including, without limitation, grafting, immobilization, electrovalent attachment, covalent attachment, adsorption, van der Waals attachment, etc. A preferred attachment mechanism is to covalently attach the nucleic acid sequence to the photoluminescent material. The attachment may be to directly attach the nucleic acid to the photoluminescent material or may be to indirectly attach the nucleic acid to the photoluminescent material, such as by interposing a linker or adhesion promoter.

The single stranded nucleic acid in a preferred example according to the invention is provided directly or indirectly on a substrate 1 (FIG. 2(a)), the substrate not being particularly limited. A reflecting or nonreflecting substrate may be used, with a nonreflecting substrate being preferred. The substrate 1 is not particularly limited and may be selected based on the end-use probe method. A substrate is not required to be used in the present invention.

The photoluminescent material used in the invention is one which allows for observing the differential optical activity when the DNA layer changes from single to double stranded nucleic acid sequences attached thereto. The photoluminescent material for use in the present invention is any material that has different optical behavior when the single stranded nucleic acid sequence attached thereto is unbound or bound. Examples of such photoluminescent materials are aromatic molecules, such as polystyrene or other polymers (all aromatic polymers will exhibit photoluminescence). The photoluminescent material used in devices according to the present invention obviates the need for photoluminescent tagging of biological sample material. The photoluminescent material (such as a polymer) to be used in the invention is selected so that when coupled with a single stranded nucleic acid and its double stranded nucleic acid, different photoluminescence is observed. Preferred photoluminescent materials are those which permit measurement of change in optical properties (i.e., complex refractive index) of the DNA as it changes from single to double stranded based on intensity of fluorescent emission from the photoluminescent material attached to a nucleic acid. A preferred example of a photoluminescent material for use in the present invention is polystyrene. In the case of polystyrene coupled with dsDNA or ssDNA, the absorption of ssDNA is higher than dsDNA in the 260 nm range, as may be observed from intensity of fluorescent emission.

The photoluminescent material may be a nanocomposite, a thin film loaded with sub-micron to nano-scale photoluminescent particles, photoluminescent particles present in a polymer matrix, or any other form of photoluminescent material.

A nanocomposite for use in the invention preferably comprises a polymer matrix encapsulating photoluminescent particles. The polymer matrix encapsulating the photoluminescent particles preferably is non-wetting such that no nucleic acid adsorption other than the intended nucleic acid attachment occurs.

However, the surface may be selectively modified to allow for controlled nucleic acid grafting where the density of molecules per unit area can be regulated. The attachment density preferably is low enough to avoid entanglement of adjacent chains and to allow for enough chain mobility for fast hybridization kinetics in solution. Preferably the density should be high enough for large change in complex refractive index of the nucleic acid layer as it changes from single stranded to double stranded. Polystyrene is an example meeting these criteria.

Preferred production methods for making devices according to the present invention include nanocomposite production procedures, self-alignment production procedures, nano-particle nano-array fabrication, and polymer blob/nanoparticle fabrication.

Figure 4A:
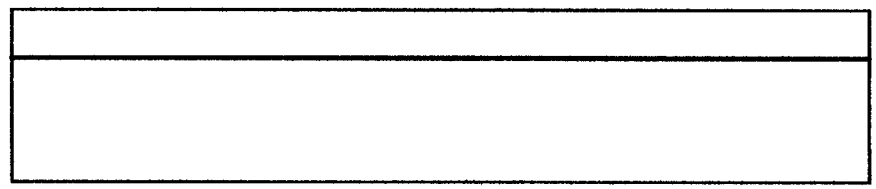
FIGS. 4(a), (b), (c) and (d) depict device fabrication with in-situ nanocomposite formation according to the invention.
Figure 4B:
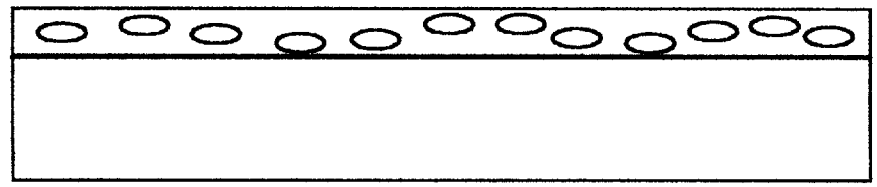
Figure 5:
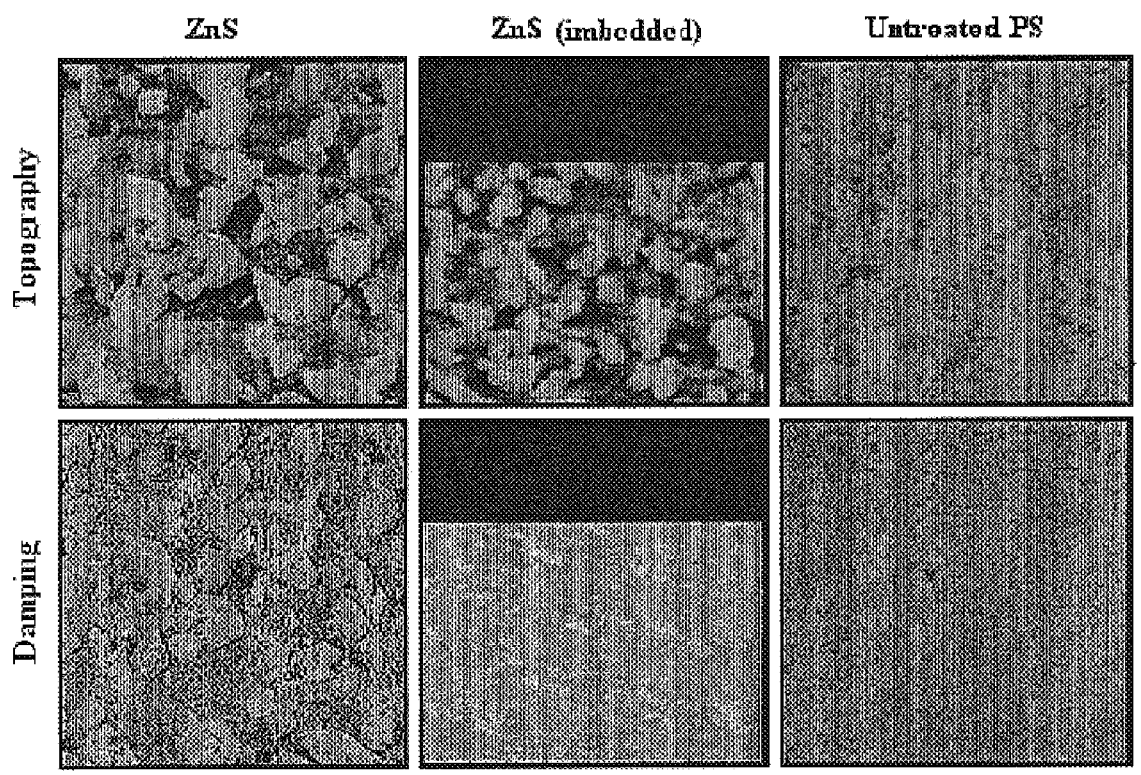
FIG. 5 shows an Atomic Force Micrograph of a nanocomposite structure according to the invention.

An example of a nanocomposite production method is as follows. As shown in FIG. 4(a), a nanocomposite film is deposited on a rigid substrate (such as quartz or glass). To deposit a smooth nanocomposite film shown in FIG. 4(b), an in-situ three-step procedure is used, in which surface modification is followed by ion exchange with an appropriate metal salt. Next, the ions are subsequently embedded and then exposed to reactive media to form photoluminescent particles. During the particle-embedding, the polymer surface is regenerated. The resultant structure is shown in FIG. 4(b), with FIG. 5 showing an Atomic Force Micrograph (AFM) of a nanocomposite structure corresponding to FIG. 4(b) and according to the invention. The surface studied is 1 by 1 µm in tapping mode where both the topography (i.e. contrast is height) and damping (i.e., contrast is local hardness) are mapped. Comparing the three types of samples clearly indicates that the particle are formed and the embedded particles are smaller than when the sulfonation takes place without any diffusion of ions in the bulk. The fact that the contrast is weaker for the embedded samples in the damping-map indicates that the particles are diffused inside and the surface is nominally all polystyrene.

Returning to the operations of FIG. 4, the regenerated surface (such as a polystyrene surface) shown in FIG. 4(b) next is selectively modified. The modification process preferably is one that (i) is selective; (ii) permits the density of functionalities on the surface to be regulated; and (iii) provides a functionality such that the 3' or 5' end of the DNA can be grafted. Simple plasma surface modification and standard wet-surface modifications are known to those skilled in the art, and either modification procedure may be used as a surface treatment in the present invention.

Figure 4C:
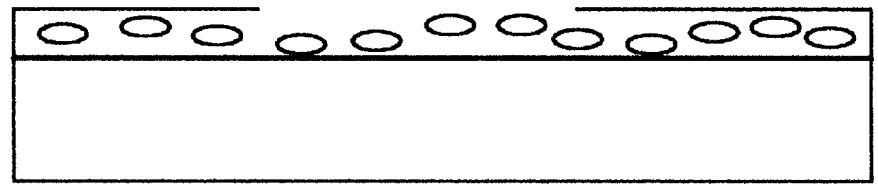
Figure 4D:
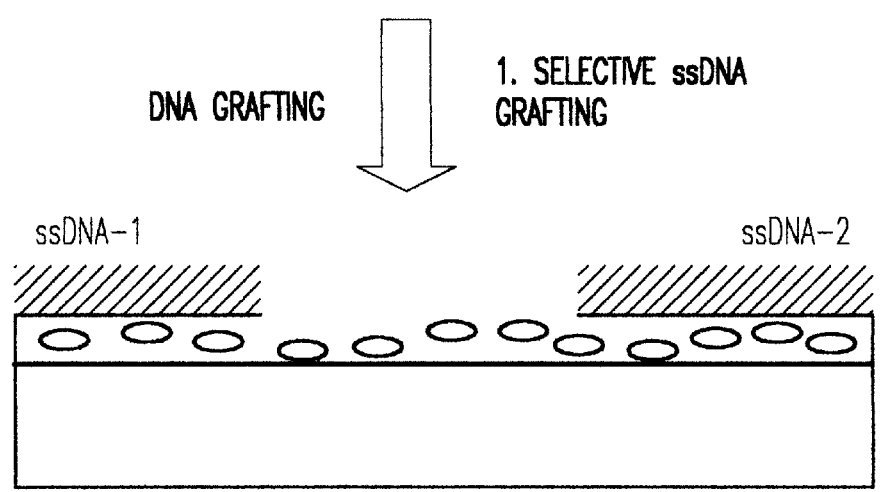
Figure 6A:
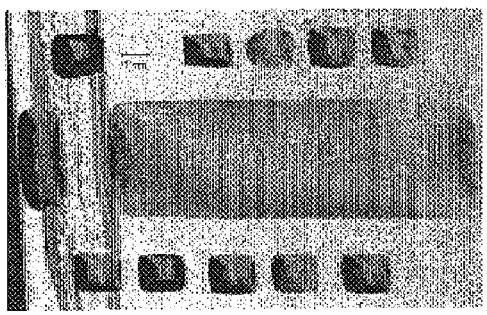
FIGS. 6(a) and 6(b) show an optical micrograph of a selectively modified polystyrene surface according to the invention.

Referring to FIGS. 4(c) and 4(d), DNA grafting may be achieved by simple dispensing of ssDNA solution on the functionalized area. As seen with reference to FIG. 6, the droplet placement of different ssDNA solutions will be self-aligning because the functional polar region is surrounded by non-polar area. FIGS. 6(a) and (b) are optical micrographs of a selectively modified polystyrene surface according to the invention. The treatment time was 90 seconds to ensure full modification. The droplets were formed by immersing the sample in water and air blowing the excess water. The scale indicator is 1 mm.

The self-alignment property is important in lowering the cost of device fabrication. For example, if 100×100 µm features at 1 mm period are made on a 25×25 mm substrate, over 600 combinatorial can be simultaneously performed. Such deposition geometry can be performed by existing dispensing systems common in microelectronics manufacturing or by micro-pipetting. The former is especially preferred because the process can be expedited to the order of 600 depositions in less than 100 seconds, with reliability. FIG. 4(d) shows the resulting surface with portions of two different types of ssDNA labeled ssDNA-1 and ssDNA-2.

FIG. 4 thus shows in-situ nanocomposite formation according to the invention, starting with a highly smooth polystyrene film deposited on a substrate. The film is then processed in three steps to produce photoluminescent particles, with ZnS:Mn particles produced. The surface is regenerated to produce polystyrene at the surface. The film is exposed to similar surface modification to functionalize the surface with acidic or basic moieties to attach to the 5' or 3' end, respectively.

As shown in FIG. 2(a), onto a substrate 1 optionally there is provided a gold electrode 4. After forming the electrode 4, a nancomposite comprising a polymer and photoluminescent particles is formed on the substrate 1 and electrode 4. A solution of polymer and photoluminescent particles may be used. As examples of the photoluminescent particles may be mentioned particles that when exposed to UV light (about 265 nm wavelength), emit visible light (e.g., green), such as ZnS doped with Mn (i.e., ZnS:Mn).

In an embodiment in which a nanocomposite is used as the optically active layer 2, nanocomposite is formed on the substrate. With reference to FIG. 1, ssDNA 3 is grafted onto the nanocomposite. Preferably, the nanocomposite surface has been modified to allow for selective grafting thereon of ssDNA. The selective modification makes possible fabricating a chip with large combinatorial of ssDNA that can be used with simple micropipette dispensing.

After any optional pre-grafting surface modification, the ssDNA 3 layer is grafted, such as by an appropriate coupling linkage, such as difunctionalized organic compounds where one end will react with a (surface modified) polystyrene surface and the other end will attach to the 3' or 5' end of the ssDNA. Examples of such organic compounds are commercially available from Sigma Chemical Co. (St. Louis, Mo.) and Molecular Probes, Inc. (Eugene, Oreg.).

Preferably the functional groups are highly polar to achieve selectivity. By functionalizing discrete regions of the polymer surface, the ssDNA can be grafted "locally" confined to these regions. Preferably these regions are about 100 by 100 microns so that it will be convenient to micropipette different ssDNA sequences in different surface modified regions. Thus an array of known ssDNA of various sequences can be deposited on the substrate 1. Because the functionalized surface is highly polar and the polymer (such as polystyrene) is non-polar the DNA solution will self align on the functionalized regions due to surface tension.

The ssDNA 3 that is grafted to the optically active polymer support is known. In a preferred embodiment, the ssDNA 3 consists essentially of a monolayer of ssDNA. The known, grafted ssDNA 3 layer is available for binding with molecules in a sample, such as hybridizing with unknown ssDNA of a sample. The amount of emitted visible light increases monotonically with the difference in reflectivity of the DNA layer as it changes from single to double stranded. The difference in reflectivity increases monotonically with change in complex refractive index from ssDNA to dsDNA.

With reference to FIG. 1, the completed structure is composed of two active layers: the top layer of grafted ssDNA 3 over a nanocomposite which is the optically active layer 2 composed of photoluminescent particles. The nature of the substrate 1 and other structure depends on the end-use probe method, such as reflection mode or transmission mode.

In an alternative embodiment of the invention, the optically active layer 2 of the device of FIG. 1 instead of being a nanocomposite is a photoluminescent polymer. Such a device may comprise a two-layer structure of a monolayer of ssDNA grafted onto a polymer thin film. The polymer thin film may be one that is optically active such that it has fluorescence when excited by radiation in the UV region, preferably in the vicinity of 265 nm wavelength. For example, the film may comprise polystyrene. The film may be deposited on an appropriate substrate depending on the intended end-use of the probe application. When the device is exposed to UV light (~265 nm wavelength), the photoactive polymer film will emit light and the device may be used as set forth above for a device in which the optically active layer 2 is a nanocomposite.

Figure 7:
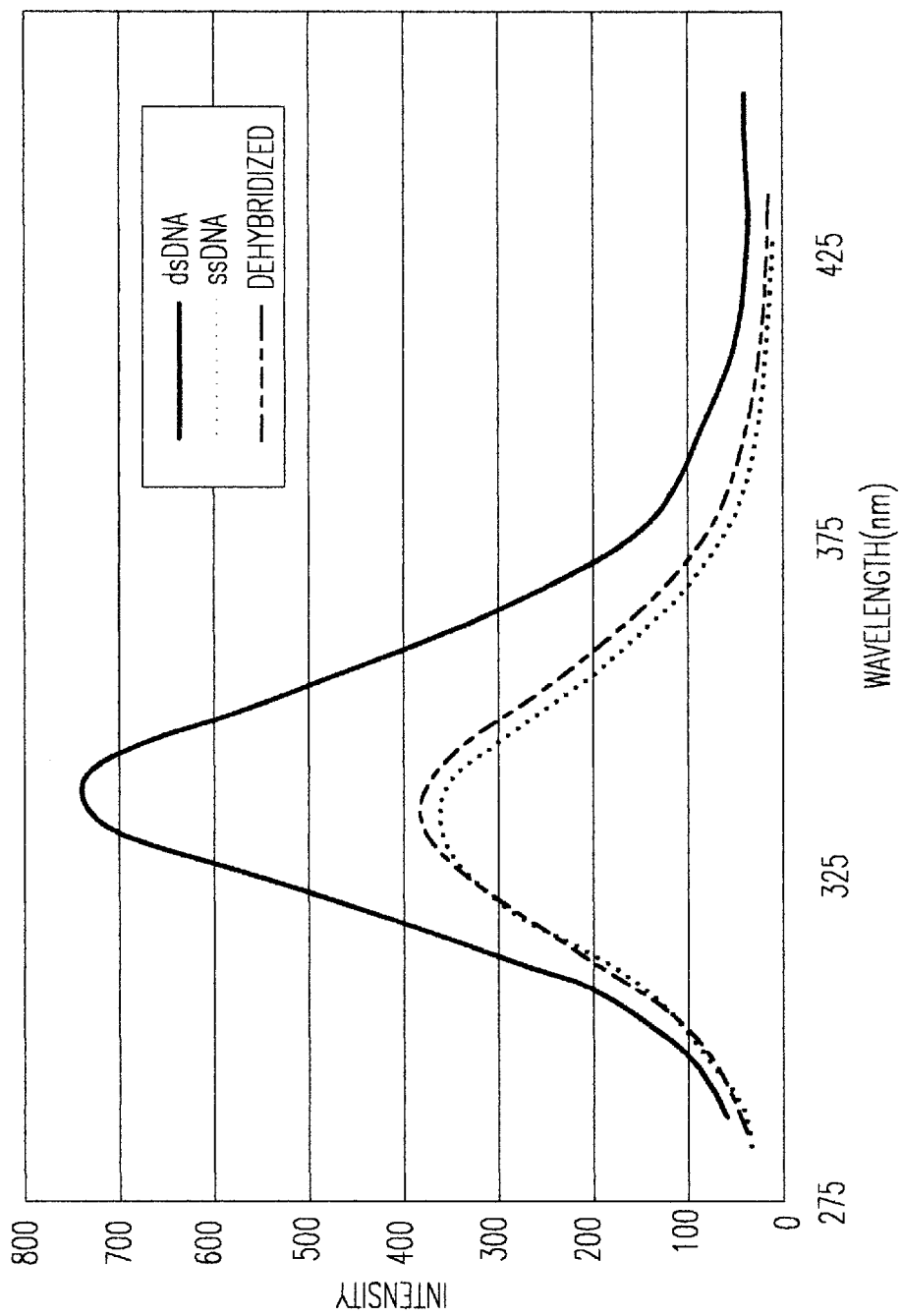
FIG. 7 shows fluorescent spectra from polystyrene used in a photoluminescent-polymer containing embodiment of the invention.

FIG. 7 shows typical fluorescent spectra from polystyrene under various conditions, when used in a device according to the present invention. The dark curve with lower intensity is the luminescence spectra of polystyrene coated with a monolayer of ssDNA. The signal is intensified as the ssDNA is converted to dsDNA. The peak intensity increases and the peak position is red-shifted. The difference in the intensity of the fluorescent light before and after the conversion of ssDNA to dsDNA is defined as the contrast. The typical contrast shown in FIG. 7 is significant to decipher the ssDNA to dsDNA transformation. This change in intensity (i.e., contrast) of the emitted light may be recorded by several methods, such as (i) a confocal microscope via a CCD camera; and/or (ii) a fiber-optic method. A fiber-optic integrated optics approach will allow for on-line measurement during the hybridization process in solution.

Fabrication of a photoluminescent polymer-containing device may be as follows. A surface modification method may be used, to allow for selective grafting of ssDNA on the polymer surface. Particularly, the selective modification allows fabricating a chip with large combinatorial of ssDNA using simple micropipette dispensing. With reference to FIG. 2(a), the structure is composed of two active layers: the top layer of grafted ssDNA over an optically active material layer which in this embodiment is a fluorescent polymer layer. The nature of the substrate and other structure depends on the probe method. Two typical, but not limiting, probe methods are: (i) in the reflection mode, there is a third layer of reflective Au to deflect the visible light produced by the photoluminescent material on topside of the device; (ii) in the transmission mode (such as primarily for device characterization), the Au layer is not included and the visible photoluminescent light is detected on the other side of the sample.

The photoluminescent polymer may be composed of a fluoescent polymer or blend of a polymer with a photoluminescent dye. The ssDNA in the top layer are of known sequence using an appropriate coupling linkage, such as difunctionalized organic compounds where one end will react with (surface modified) polystyrene surface and the other end will attach to the 3' or 5' end of the ssDNA.

Figure 6B:
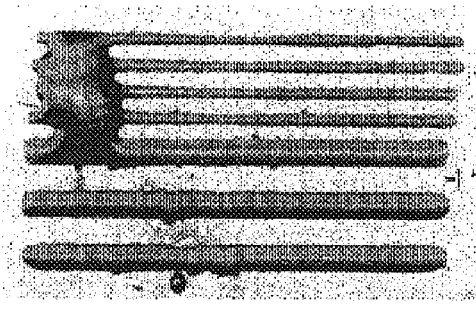

It is preferred that the functional groups are highly polar to achieve selectivity. By functionalizing discrete regions of the polystyrene polymer, the ssDNA can be grafted locally confined to these regions. It is preferred that these regions are about 100 by 100 microns making for convenient micro-pipetting of different ssDNA sequences in different regions. Thus an array of ssDNA of various sequences can be deposited on the polystyrene substrate. Because the functionalized surface is highly polar and the polystyrene is non-polar, the DNA solution droplets will self-align on the functionalized regions due to surface tension. FIGS. 6(a) and 6(b) show such a surface modified polystyrene film according to the invention. After immersing the film in water only the modified area has a wetting characteristic.

Preferably, the polymer for layer 2 is selected to be non-wetting such that no DNA adsorption is possible. However, selective modification of the surface may be used to allow for controlled ssDNA grafting where the density of molecules per unit can be regulated. Thus, even if a drop is too big, the drop will confine itself to the selectively modified area. The graft density preferably is low enough to avoid entanglements of adjacent chains and to allow for enough chain mobility to allow for fast hybridization kinetics in solution. Also, the density preferably is high enough to result in a large absorption by the DNA layer. One exemplary polymer that fits these criteria is polystyrene. FIGS. 6(a) and 6(b) show selective modification of polystyrene, with only the area exposed being wetting and suitable for single stranded nucleic acid strands to graft thereto.

Thus, a DNA chip according to the invention may be fabricated using self-assembly techniques, which are less expensive than lithography used in traditional methods of making DNA chips. Self-assembly is significantly less expensive than traditional lithography-based DNA chip fabrication methods. The self-alignment property of ssDNA is exploited, particularly, the functional polar region being surrounded by non-polar area. A reliable and relatively fast manufacturing process may be accomplished, with many depositions per minute possible.

Another alternative for making devices according to the present invention is to decorate nanoparticles on a block copolymer template. A block copolymer comprising at least two chain types is deposited on a substrate. The deposition is performed either by a solution process or a solid-forming process. The block-copolymer film is thermally processed to separate the nanophase into discrete phases of the minority polymer. The structure of the discrete phase may be nanospheres or cylinders with nano-scale diameter or other (more) complex geometries depending on constituents of the block copolymer. The important property of the film is a structure with phase-separated regions with characteristic dimensions in the 5–500 nm scales.

Next, the block copolymer is subjected to a surface treatment that etches the surface to expose the discrete phase and in the same process activates the surface of the discrete phase. However, the etched "matrix" polymer is not activated. Subsequently, the structure is exposed to precursor solution of inorganic and/or organo-metallic salts in a solvent system that does not attack the block copolymer. The salt(s) react with the activated surface to form a selective deposition on the exposed surface of the discrete phase.

Next, the deposited salt is reacted either with a reactive gas or an active solution to form nanoparticles that are specifically confined to the discrete phase regions. The sample optionally may be annealed before or after the nanoparticle synthesis step. Annealing embeds the resultant nanoparticles in the discrete phase. The resultant structure is defined as polymer blobs with nanoparticles.

Figure 14A:
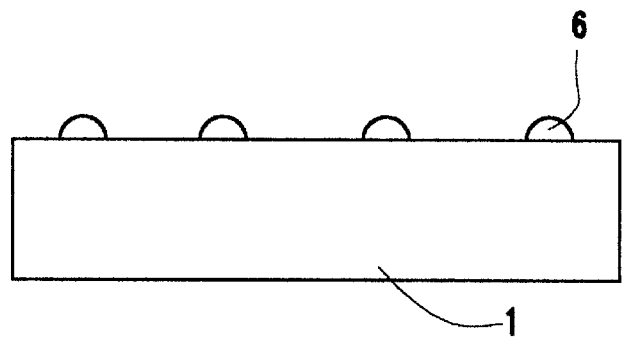
FIGS. 14(a), (b) and (c) are a series of cross-sectional drawings showing fabrication of a polymer blob/nanoparticle embodiment of the invention.
Figure 14B:
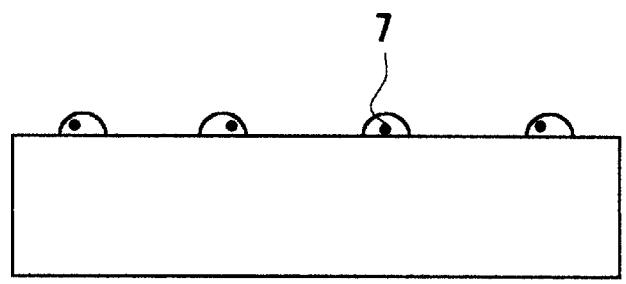
Figure 14C:
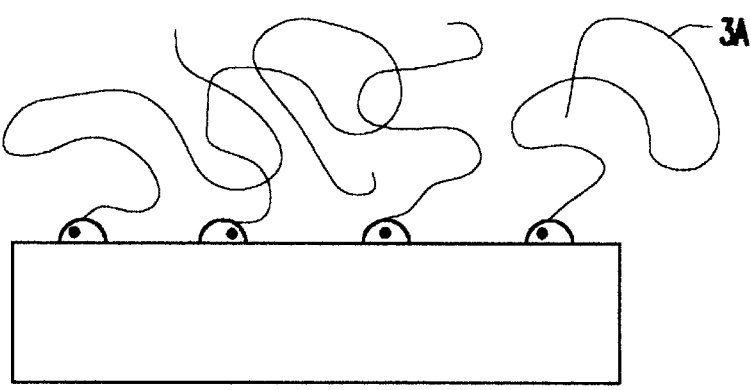

FIG. 14 shows a schematic of an exemplary process flow to make a chip according to the invention. Polymeric "blobs" 6 ranging in size from about 10–1000 nm are produced on a substrate 1. The blobs may be on a random or periodic array (see FIG. 14(a)). Subsequently a single stranded nucleic acid molecule 3a is attached (such as by grafting) to each blob 6. Depending on the size of the blob and the number of bases in the nucleic acid sequence 3a, the number of nucleic acid sequences 3a per blob 6 may range from about 1 to 10. For blob diameters below 50 nm and nucleic acid molecules having more than 80 bases, the number of nucleic acid molecules is likely to be one per blob.

FIGS. 15(a)–(g) show an exemplary method of fabricating a nucleic acid chip according to the invention. As FIG. 15(a) shows, as starting materials, on a substrate 1 is provided a block copolymer 8 in which one of the blocks 8B is a diene polymer that may be etched by an oxidation process such as ozone or oxygen plasma. The other polymer segment 8A is an ozone resistant polymer. Polymer segment 8B is the majority phase and polymer segment 8A (shown as spherical) is the minority phase. The composition is such that the minority phase 8A separate to form spheres or sphere-like particles. It is preferred that the block copolymer 8 is fairly monodispersed to have the spheres self assemble in a nominally regular lattice. As an example, minority phase polymer segment 8A may be polystyrene (PS) or poly (methyl methacrylate) (PMMA) and majority phase 8B may be polyisoprene or polybutadiene.

In FIG. 15(b), the block copolymer thin film 8 is spin cast and annealed to form a monolayer of the microphase separated spheres. Then the matrix is etched by ozone or plasma to form isolated A-spheres 8a. Subsequently the sphere 8a is annealed above the glass transition temperature of the polymer to form polymer "blob" 88 (see FIG. 15(c)). In the next step, the surface 1a of the substrate 1 is modified by anionic groups (see FIG. 15(d)) to provide modified blobs 88a. The group used for such modification may be a strong anion that forms a salt when exposed to an aqueous solution of Zn, Cd, Pb or Hg salts. Upon annealing (see FIG. 15(e)) to form annealed blobs 88b and exposure to $H_2S$, II–VI calcogenid nanoparticles 9 will be formed (see FIG. 15(f)) in the blobs 88c. To provide the highest photoluminescence, a typical nanoparticle may be doped, such as, ZnS:Mn or ZnS:Ag. The former has highest photoluminescence intensity around 265 nm which is close to the maximum absorption of nucleic acids in the UV-region.

Figure 16A:
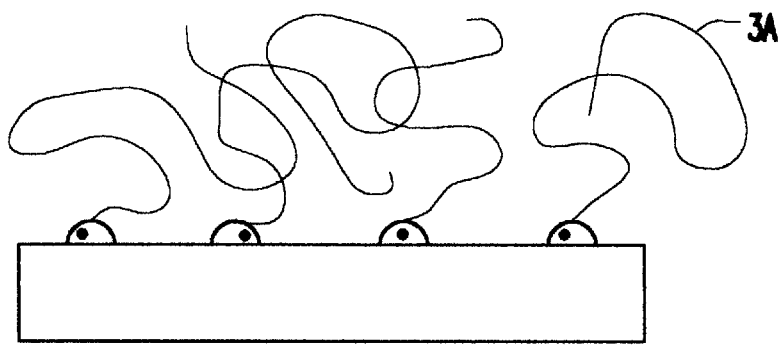
FIG. 16(a) shows an exemplary structure of a nanoparticle/polymer blob bio-chip according to the invention before use.
Figure 16B:
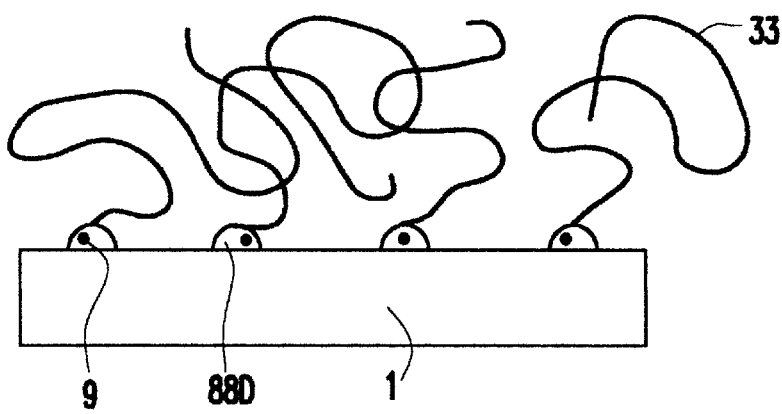
FIG. 16(b) shows the structure of FIG. 16(a) after the single stranded nucleic acid has hybridized with a complementary base sequence to form a double stranded nucleic acid.

In the next step, the blob surface is modified again by wet chemistry, plasma or corona to form moieties that can react with the 3' or 5' end of the nucleic acid chain. For example, if a hydroxyl group is formed by water plasma, the phosphate end will react to form a covalent bond. Thus the nucleic acid chain will be grafted on the polymer blob surface. Depending on the size of the nucleic acid, one or more chains can be grafted per blob. For a long chain over 50 bases, only one chain may be grafted per blob due to the lateral size of the chain (see FIG. 16(a) which is an enlargement of FIG. 15(g)). FIG. 15(g) and FIG. 16(a) show a final structure with a nanoparticle 9 in a blob 88d and the single stranded nucleic acid 3a graft. When such a surface is exposed to a mixture of single stranded nucleic acid fragments, the probe single stranded nucleic acid grafted on the substrate will act like chemical tweezers to pick the complementary single stranded nucleic acid for hybridization. The resultant double stranded nucleic acid 33 on the surface is shown in FIG. 16(b). Nanoparticles 9 generally have a diameter in the range of 2–30 nm. Blobs 88d generally have a diameter of about 10–100 nm and pitch about 10–100 nm.

Figure 17A:
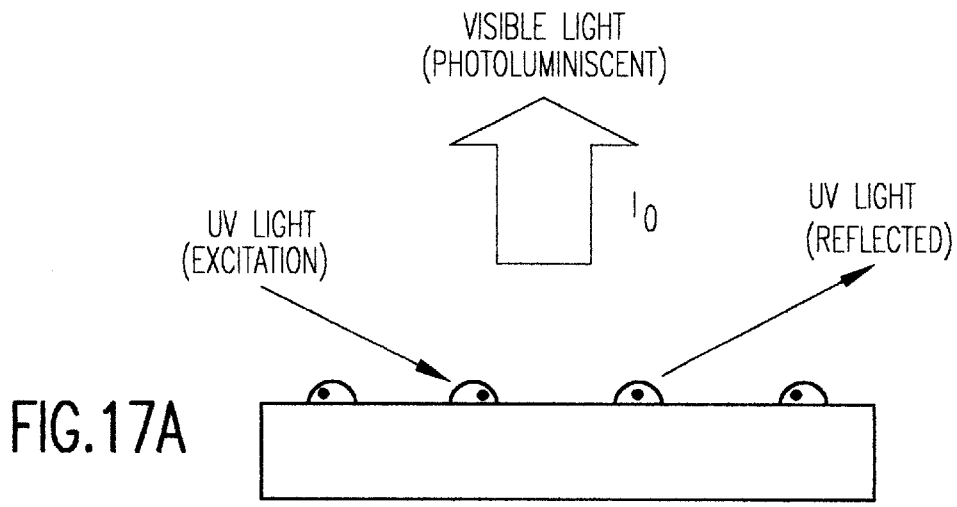
FIGS. 17(a)–(c) show a reading method according to the invention for the device of FIGS. 16(a)–(b), in which UV light is incident at an angle on the sample and the luminescent visible radiation from nanoparticles is recorded.
Figure 17B:
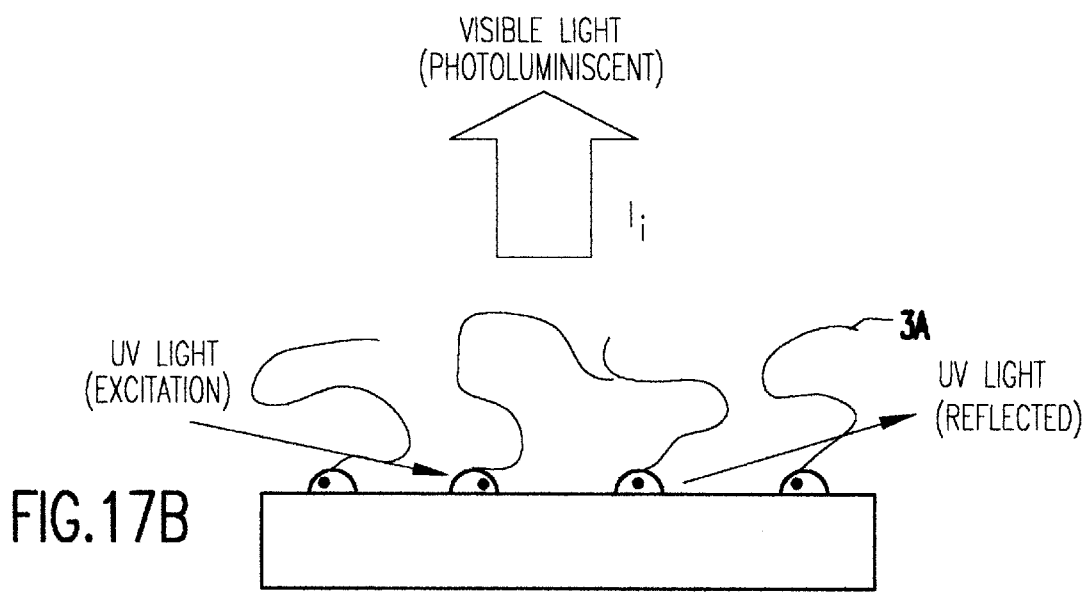
Figure 17C:
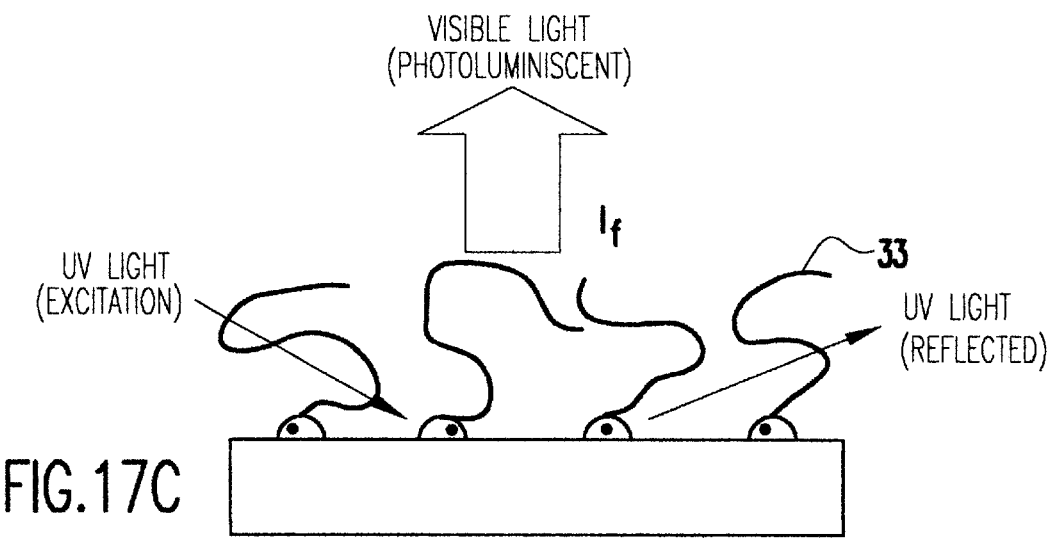

For a device such as that of FIGS. 16(a)–(b), a reading method may be provided as follows. The reading of the hybridized sites indicating a match is explained in FIGS. 17(a)–(c). When the chip with no nucleic acid is exposed to UV light (excitation light or probe light) the photoluminescent nanoparticles radiate $I_0$ in the visible range (see FIG. 17(a)). The visible light is equal in all directions. To avoid any interference from the probe (i.e., UV) light, the luminescence intensity $I_0$ is recorded in the normal direction. When the nucleic acid chip with single stranded nucleic acid 3a is exposed, the intensity changes from $I_0$ to $I_1$ because the light incident on the nanoparticle changes due to change in the optical property (i.e., absorption, reflectivity or scattering) of the top surface due to attachment of the single stranded nucleic acid (see FIG. 17(b)). The intensity further changes to If when the single stranded nucleic acid hybridizes to form double stranded nucleic acid 33 (see FIG. 17(c)). The change from FIGS. 17(b) to 17(c) is due to the change in complex refractive index of DNA as it converts from single to double stranded. Thus the amount of photoluminescent light from the nanoparticle will change accordingly in the three cases shown in FIG. 17. The contrast, $I_i$–$I_0$ is proportional to the number of single stranded nucleic acid molecules per unit area. Hence a calibration of the sites available for hybridization will be provided. The contrast $I_f$–$I_0$=$\Delta I$ is proportional to the number of single stranded nucleic acids hybridized to double stranded.

The production methods discussed above are by way of example, and are not limiting. For example, where ssDNA is mentioned, the methods may be applied for other nucleic acids.

Figure 13:
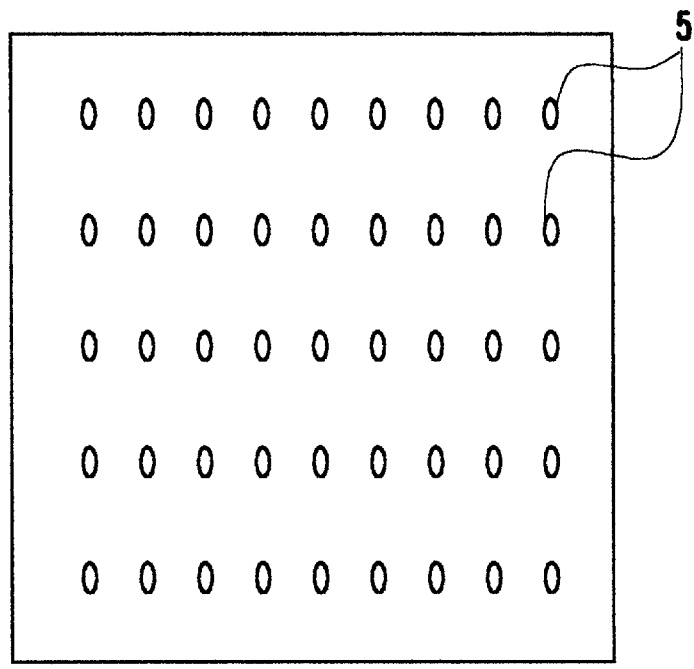
FIG. 13 shows a top view of a bio-chip according to the invention

Using any of the above-mentioned production methods, or any other suitable method, a bio-chip such as that of FIG. 13 with an array of pixels 5 may be made. In a preferred embodiment, the invention provides a DNA chip for photoluminescent measurements at $10^4$ pixels (sites). The same pixel may be repeated 100 times, at different locations, so that repeated measurements may be made, to establish statistical significance. For example, a $10^4$ $\mu m^2$ size probe with structure shown, for example, as in FIG. 16(a) may be fabricated. Each substrate may have a different single stranded nucleic acid probe. The UV light input and visible light out may be coupled in to the substrate by a typical integrated optical method, known to one skilled in the art. For example, optical fibers may be used. To improve the signal to noise ratio the incident beam may be modulated and the output signal may be locked-in at the same frequency. Such an integrated approach advantageously builds an on-line sensor where each fiber or fiber bundle has a type of single stranded nucleic acid different from the other fiber bundle. In this way, several single stranded nucleic acids may be probed in a mixture simultaneously, such as in a multi-gene probe.

A "digital" approach may be used in fabricating a bio-chip according to the invention, in which the probe sites are arranged on a periodic array with 10–50 nm scale periodicity. A discrete, periodic arrangement will allow for absolute nucleic acid count with high sensitivity and accuracy, and low noise/error that otherwise arises due to overlap of signals from adjacent fragments in an "analog" method. Compared to conventional bio-chip technologies, the inventive methods and products are useable with sample sizes $10^3$–$10^4$ smaller. Also, the array fabrication may be based on a relatively inexpensive and highly parallel self-assembly approach instead of expensive lithographic techniques.

The present invention has been discussed above particularly with regard to nucleic acids. Because the complex refractive index of the proteins also changes significantly in the UV range as it reacts with other proteins or alters structure, a sensor or analytical device can be fabricated to probe antigens and proteins as discussed above with regard to nucleic acids. Thus, an antigen-antibody sensor may be provided. In such a device, the desired antibody replaces the single stranded nucleic acid. Because no tagging is required, such a device can be a highly sensitive sensor to detect small levels of antigens and proteins that are airborne or in liquid. The principle of detection and device fabrication is as set forth regarding the use of single stranded nucleic acids.

Non-limiting examples according to the invention are as follows.

EXAMPLE 1

Figure 8:
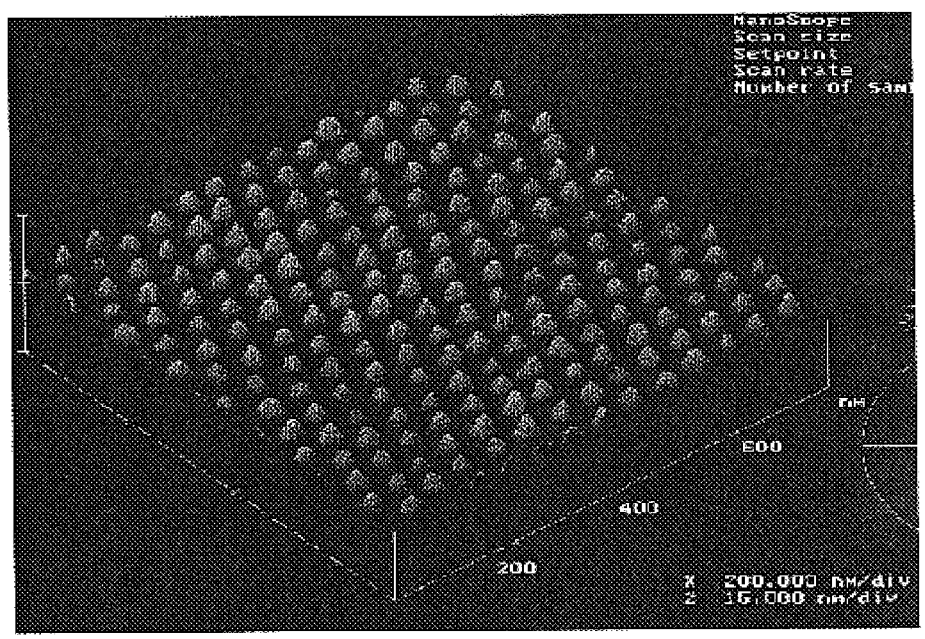
FIG. 8 shows a monolayer of polystyrene/polybutadiene block copolymer spheres on an exemplary silicon surface according to the invention.
Figure 11:
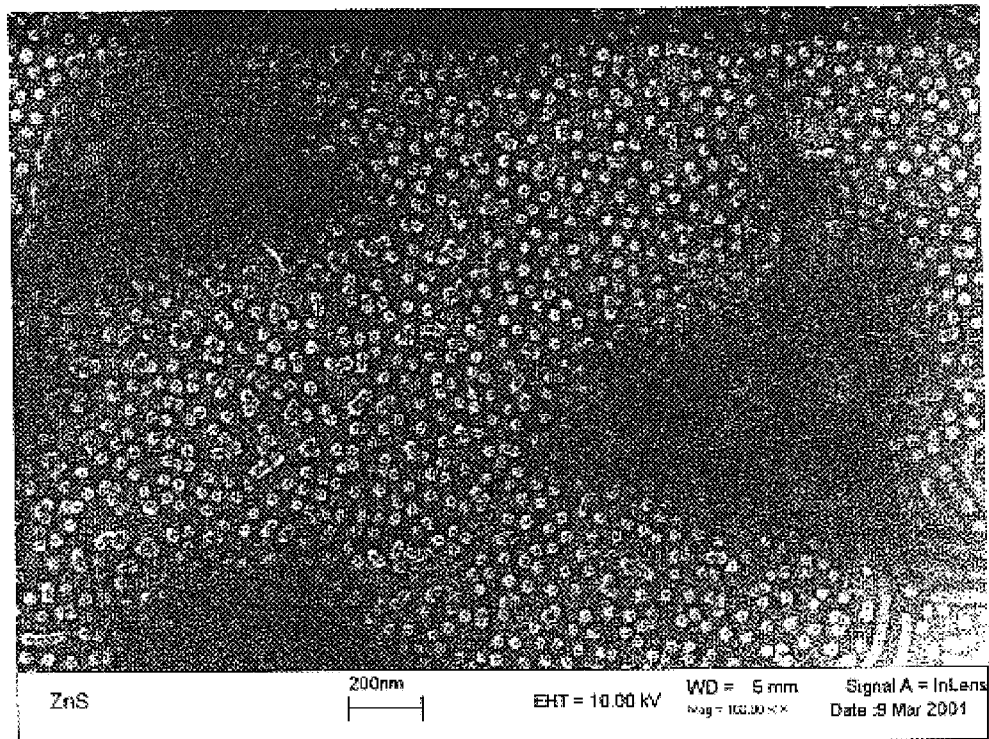
FIG. 11 is a field emission micrograph of ZnS nanoparticles on a block copolymer-based exemplary material according to the present invention.
Figure 9:
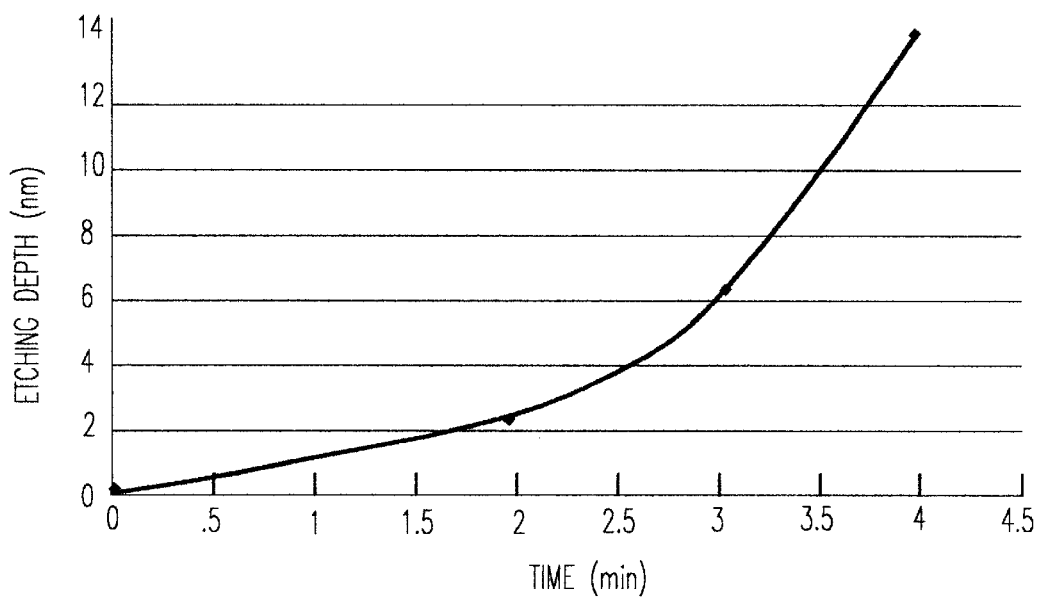
FIG. 9 is a graph of etching behavior of polybutadiene as a function of exposure time for an exemplary block copolymer according to the present invention.
Figure 10:
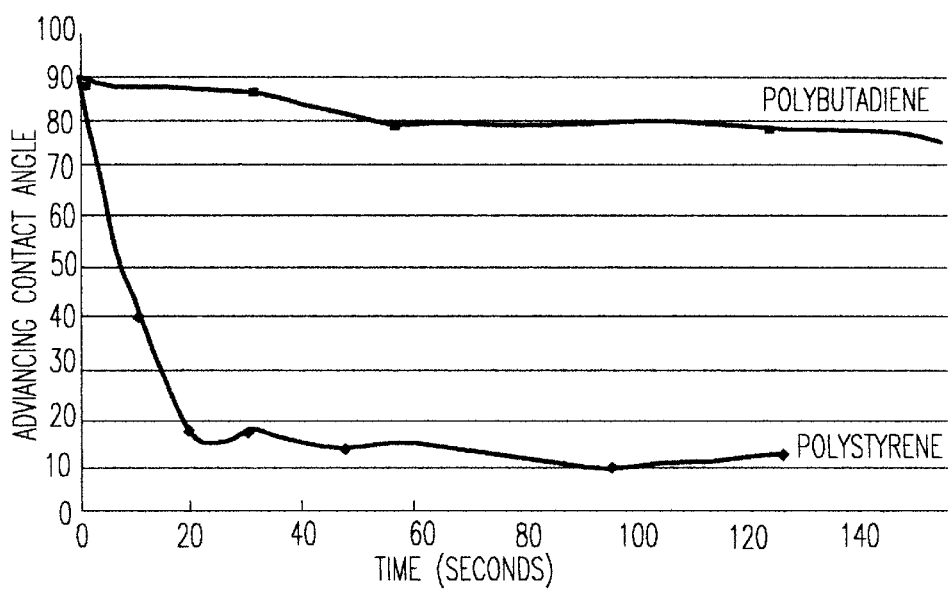
FIG. 10 is a graph of the effect of surface treatment on contact angle of water, for exemplary materials according to the present invention.
Figure 12:
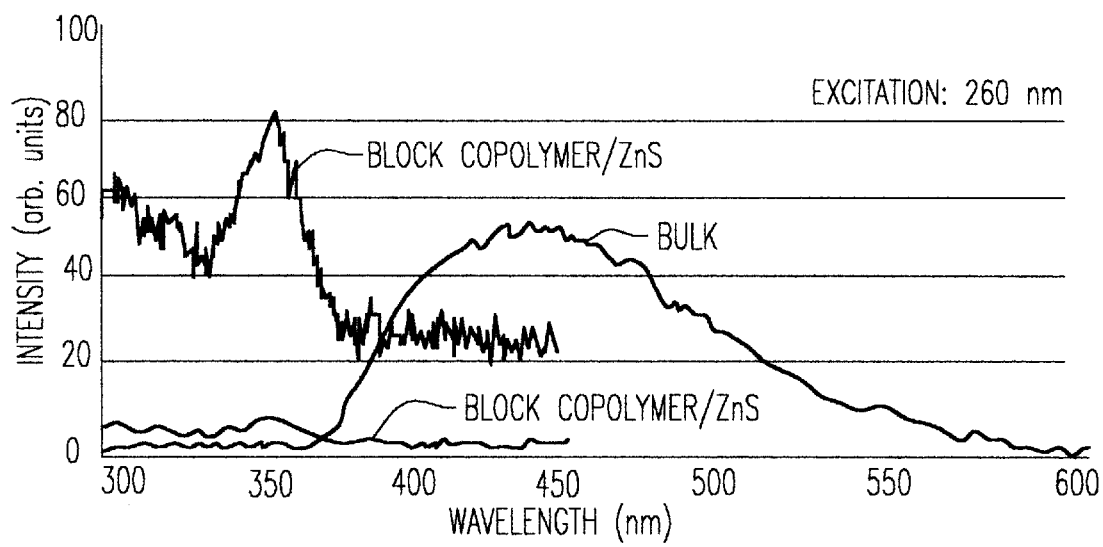
FIG. 12 shows photoluminescence spectra for ZnS-containing materials according to the present invention.

A block copolymer film of polystyrene (PS)/ polybutadiene (PB) was deposited on a silicon (Si) surface to produce a highly ordered discrete phase of PS spheres. See FIG. 8. The structure was then exposed to plasma containing water vapor to etch the butadiene and modify polystyrene. FIG. 9 shows a typical etch curve (for polybutadiene) indicating the amounts of etch as a function of exposure time. To confirm that the surface modification is indeed selective, pure polymer PS and PB were exposed to similar treatment. The wetting angle for water, in FIG. 10, as a function of plasma exposure clearly indicates that PS is modified and becomes highly polar (i.e., wetting) however, PB is not modified in any significant manner. Particularly, FIG. 10 shows that the contact angle of water decreases on PS but remains high for PB as the treatment time increases. The activated surface is immersed in Zn-salt solution and exposed to $H_2S$ to form ZnS. FIG. 11 shows a typical field-emission scanning electron micrograph (SEM) where the PS spheres are bright compared to the PB matrix. The brightness of PB is attributed to presence of high atomic number Zn compared to low atomic weight materials (i.e., C and H) in the matrix. In FIG. 11, ZnS nanoparticles on a block copolymer are shown, and notably the PS discrete islands are spherical and bright compared to the matrix indicating that the ZnS is confined only to PS. The random arrangement of PS spheres is due to over-etching of PB. Photoluminescence (PL) spectra of the resultant sample shown in FIG. 12, which shows photoluminescence from ZnS particles, indicate that the typical emission peak at ~420 nm is strongly blue shifted by over 100 nm indicating the presence of nanoparticles of ZnS. The strong blue shift is an indication of quantum confinement effects indicating a nominal size of <3 nm ZnS particles.

EXAMPLE 2

Using self-assembled block copolymer monolayers and high anisotropic etching, a structure is made by grafting ssDNA fragments (x) on a nanoparticle coated polymer blob. The blobs (made of polystyrene (PS)) are arranged periodically on a (silicon) substrate. The periodicity and size of the blobs is in the 10–20 nm range (see FIG. 14(a)). The direct band gap semiconductor nanoparticles are embedded in-situ in the polymer to ensure nominally monodispersed size distribution and to simplify the process. The luminescence excitation will be tailored to the maximum at ~260 nm (close to the absorption maxima of DNA). As the ssDNA is grafted, the luminescent light in the visible range will be attenuated from $I_0$ to $I_f$. Thus by measuring the difference $\Delta I = I_f - I_i$ as the probe sites with x grafts are exposed to a ssDNA mixture the amount of y fragments can be quantitatively calculated. The calibration constant relating $\Delta I$ and number of y attached to the substrate is determined exactly since the number of x sites are known. To achieve measurable contrast, i.e., $\Delta I \sim 10\%$ change, the minimum ssDNA size is a 50 base pair sequence. For 50 base sequence ssDNA on 20 nm pitch array, only one chain per blob is possible due to lateral size of the gaussian chain (see FIG. 14(a)). A total array size of $10^4 \, \mu m^2$ is sufficient to measure $I_0$, $I_i$ and $I_f$ for nanoparticle monolayers with a conservative quantum efficiency of 25% and detector acceptance angle of 30°. This way, a sensitivity to measure $2.5 \times 10^7$ ssDNA (or ~10 femotgram) per array is possible. By making an ensemble with several arrays of different ssDNA grafts and connecting each array to a 100 $\mu$m diameter optical fiber, a parallel analysis of several fragments can be achieved.

While the invention has been described in terms of its preferred embodiments, those skilled in the art will recognize that the invention can be practiced with modification within the spirit and scope of the appended claims.

We claim:

1. A tagging-free method to detect the binding of untagged single stranded nucleic acid to an untagged material of interest, comprising the steps of:
   (A) providing a sensor comprised of a first layer and a second layer wherein said first layer comprises an untagged single stranded nucleic acid and wherein said second layer comprises a photoluminescent material, and wherein said first layer and said second layer are separate layers, and wherein said second layer comprises material selected from the group consisting of aromatic polymers, doped or undoped metal oxides, sulfides, arsenides, tellurides, and nitride and phosphide nanocomposites;
   (B) exposing said sensor to a biological sample for sufficient time for said untagged single stranded nucleic acid to bind to an untagged material of interest in said biological sample;
   (C) applying light to said sensor; and
   (D) measuring photoluminescence from said sensor, wherein photoluminescence measured in said step of exposing is indicative of binding of said untagged single stranded nucleic acid to said untagged material of interest.

2. The tagging-free method of claim 1, wherein the single stranded nucleic acid is selected from the group consisting of DNA, RNA and PNA.

3. The tagging-free method of claim 1 wherein said second layer comprises a matrix material, with said photoluminescent material associated with said matrix material.

4. The method of claim 3 wherein said photoluminescent material is embedded in said matrix material.

5. The tagging-free method of claim 1, wherein the second layer comprises polystyrene.

6. The tagging-free method of claim 1, wherein the second layer comprises photoluminescent particles in a polymer matrix.

7. The tagging-free method of claim 6, wherein the photoluminescent particles are doped or undoped compounds selected from the group consisting of group II and group VI.

8. The tagging-free method of claim 7, including doped or undoped zinc sulfide.

9. The tagging-free method of claim 1, wherein the second layer comprises a nanocomposite.

10. The tagging-free method of claim 1, wherein said light is applied to said first layer of said sensor, and said light is ultraviolet light with wavelength in the range of 200–700 nm.

11. The tagging-free method of claim 10, wherein the wavelength of the ultraviolet light is in the range of 260–265 nm.

12. The tagging-free method of claim 1, wherein the first layer comprises an ssDNA monolayer.

13. The tagging-free method of claim 1, wherein the second layer comprises a thin-film or a support.

14. The tagging-free method of claim 1, wherein the second layer comprises a polymer.

15. The tagging-free method of claim 1, wherein the nucleic acid sequence is between 5 and 200 base pairs.

16. The tagging-free method of claim 15, wherein the sequence is about 25 base pairs.

17. The tagging-free method of claim 1, wherein the second layer has fluorescence when excited by light with a wavelength in the 200–700 nm range.

18. The tagging-free method of claim 1, wherein the sensor comprises ssDNA as said first layer grafted onto the second layer.

19. The tagging-free method of claim 1, wherein said first layer comprises a plurality of sections each of which comprises a different untagged single stranded nucleic acid sequence.

20. The method of claim 1, wherein said first layer is positioned on a first side of said second layer, and said measuring step measures photoluminescence from a second side of said second layer.

21. The method of claim 20, wherein said second side is opposite said first side on said second layer.

22. The method of claim 1, wherein said first layer is positioned on a first side of said second layer, and said measuring step measures photoluminescence reflected from said first side of said second layer.

* * * * *